United States Patent [19]

Glausch

[11] Patent Number: 5,156,678
[45] Date of Patent: Oct. 20, 1992

[54] COATING WITH ORGANIC DYES

[75] Inventor: Ralf Glausch, Darmstadt, Fed. Rep. of Germany

[73] Assignee: Merck Patent Gesellschaft Mit Beschraenkter Haftung, Darmstadt, Fed. Rep. of Germany

[21] Appl. No.: 673,990

[22] Filed: Mar. 25, 1991

[30] Foreign Application Priority Data

Mar. 24, 1990 [DE] Fed. Rep. of Germany ....... 4009567

[51] Int. Cl.$^5$ .............................................. C09B 67/50
[52] U.S. Cl. ...................................... 106/410; 106/415; 106/418; 106/425; 106/436; 106/453; 106/456
[58] Field of Search ................... 106/410, 417, DIG. 3

[56] References Cited

U.S. PATENT DOCUMENTS

| | | | |
|---|---|---|---|
| 3,483,190 | 12/1969 | Zickendraht et al. | 106/410 |
| 4,084,983 | 4/1978 | Bernhard et al. | 106/417 |
| 4,755,229 | 7/1988 | Armanini | 106/413 |
| 5,061,317 | 10/1991 | Korpl et al. | 106/417 |

FOREIGN PATENT DOCUMENTS 220617 5/1987 European Pat. Off. .

OTHER PUBLICATIONS

CA 101:73712x.
CA 105:8034w.
Abstract of EP 103,986-A.

*Primary Examiner*—William R. Dixon, Jr.
*Assistant Examiner*—Margaret V. Einsmann
*Attorney, Agent, or Firm*—Millen, White & Zelano

[57] ABSTRACT

Effect pigments based on interference pigments coated with phthalocyanine or metal phthalocyanine dyes, characterized in that the dyes are applied to the pigments as a strongly adhering film without the aid of binders or other auxiliary materials, are outstandingly suitable for use in formulations such as paints, dyes, plastics and cosmetics.

15 Claims, No Drawings

COATING WITH ORGANIC DYES

BACKGROUND OF THE INVENTION

The invention relates to "effect" pigments based on interference pigments coated with phthalocyanine or metal phthalocyanine dyes, the dyes being applied to the pigments as a strongly adhering film without auxiliary materials. Interference pigments owe their color to the interference effects of light passing through a translucent coating onto an opaque substrate such as a flaky mica, whereas "effect" pigments are those whose color is due both to absorption and interference effects.

Various processes are known for dyeing pigments with organic dyes, for example, simple mixing of pigment and dye (U.S. Pat. No. 4,755,229), suspending the pigment in dye solution (U.S. Pat. No. 3,311,485), grafting (EP 0,103,986) and adhesion with the aid of a binder system (EP 0,220,617).

In particular, a permanent coating with phthalocyanine dyes, has hitherto been achieved exclusively with the aid of binders, for example, polymers as described, for example, in the laid-open specifications EP 220,617 and JP 59/47,240, and in U.S. Pat. No. 4,755,229, or with coprecipitation of metal hydroxides, as described in Czechoslovakian Patent CZ 244,792.

SUMMARY OF THE INVENTION

It has now been found, surprisingly, that a permanent coating on interference pigments without participation of auxiliary materials can be achieved if a pigment suspension in the dye solution is brought together with a solvent in which the dye is essentially insoluble.

Accordingly, the invention relates to effect pigments based on interference pigments coated with phthalocyanine or metal phthalocyanine dyes, characterized in that the dyes are applied to the pigments as a strongly adhering film without the aid of binder systems or other auxiliary materials.

Accordingly, the invention also relates to a process for the production of effect pigments based on interference pigments coated with phthalocyanine or metal phthalocyanine dyes, characterized in that the dyes are applied to the pigments as a strongly adhering film without the aid of binder systems or other auxiliary materials.

Accordingly, the invention also relates to a process for the production of effect pigments based on interference pigments coated with phthalocyanine or metal phthalocyanine dyes, characterized in that a suspension of the pigment in a solution of the dye is produced and the suspension obtained is brought together with a solvent in which the dye is essentially insoluble.

The invention further relates to the use of the effect pigments according to the invention in formulations such as paints, dyes, plastics and cosmetics.

The invention finally relates to formulations which contain the effect pigments according to the invention.

The effect pigments are distinguished by a number of advantageous characteristics. On the one hand, the dye is applied to the interference pigment in the form of a strongly adhering, compact film. On the other hand, no adhesion promoter, for instance, a polymeric binder system is present. Both features in combination give rise to a permanent coating of the dye on the pigment, the inherent color of the dye resulting in very high color fastness and high depth of color even when deposited in the form of very thin films. Furthermore, the characteristic gloss of the interference pigment is almost completely retained after being coated with the dye. On the other hand, losses of gloss and weakening of the color fastness or depth of color can be observed in the conventional coatings using adhesion promoters. The effect pigments according to the invention are further distinguished by a shift of the inherent color of the pigment towards the interference color. By a suitable combination of the inherent color of the interference pigment and the inherent color of the dye, it is possible to achieve various color effects with intense hues, the finished pigment ultimately being assured of a high gloss.

Any suitable interference pigments, in particular mica flakes coated with metal oxides, known as pearl luster pigments, are suitable for the production of the effect pigments according to the invention. In principle, any common pearl luster pigments are suitable, for example, mica coatings with colorless or colored metal oxides such as $TiO_2$, $Fe_2O_3$, $SnO_2$, $Cr_2O_3$, $ZnO$ and other metal oxides, either alone or in a mixture, in a single layer or consecutive layers. These pigments are known, for example, from German Patents and patent applications 1,467,468, 1,959,998, 2,009,566, 2,214,545, 2,215,191, 2,233,298, 2,313,331, 2,522,572, 3,137,808, 3,137,809, 3,151,343, 3,151,354, 3,151,355, 3,211,602, and 3,235,017.

It is particularly preferred to use mica pigments which are coated with colorless metal oxides and which do not possess an inherent color but only an interference color. For the purpose of the coating, the pigments are then suspended in the dye solution. In this connection the choice of the suitable solvent usually depends on the dye itself. Any common phthalocyanine and metal phthalocyanine dyes known to a person skilled in the art, for example, those mentioned in EP 0,266,247, may be used. Preferred dyes are all metal phthalocyanines (MePc), wherein Me is Fe, Co, Cu, Zn, Si, Bi and Sn. Usually, a dye solution of 1 to 20% by weight dye in solvent is used. Concentrated sulfuric acid is a particularly suitable solvent for preparing the dye solution, although any solvent in which the dye is soluble may be used. Such solvents are conventional and known to one of ordinary skill in the art.

The coatings are usually carried out using about 1-3% dye, based on the total weight of pigment. If special effects are aimed at, the amount of dye may also be outside the stated range. Coatings using about 10-20% dye shift the color of the base substrates towards the blue color of the phthalocyanine dyes. In other ranges of concentration other new colors can be observed, for example, in the range of 0-0.1% dye coated pigments result with a greyish color.

The suspension of the pigment in the dye solution is then brought together with the solvent in which the dye is essentially insoluble. For example, "essentially insoluble" means a solvent which, when added to a suspension of dye and pigment results in the precipitation of a desired amount of dye from solution onto the pigment. In the case of a solution of the dye in concentrated sulfuric acid, the suspension is expediently treated by being poured into water. Generally, the dyes are insoluble in known solvents, with the exception of sulfuric acid and, to a small extent, in DMF ($c < 10^{-3}$%). In this process the dye is precipitated on the pigment in the form of a strongly adhering, compact film. The pigment is then separated by conventional processes, washed and dried. The effect pigment produced by the process according to the invention is distinguished by high gloss, improved color stability and, in particular, by the shift of the interference color towards the inherent color of the pigment and by improved dispersibility in paint systems. When coating an effect pigment with phthalocyanine dyes, the given color of the effect pigment combines with the color of the dye to produce effect pigments with new and appealing color effects. Therefore, the color depends on the concentration of the dye relative to the substrate. Desired colors can be produced with only routine experimentation by one of ordinary skill in the art.

The effect pigments according to the invention may be used in any formulations in which such pigments are used, for example, in paints, dyes, plastics and cosmetics, as disclosed in H. P. Preuss, Metal Finishing, pp. 53–58, December, 1969; C. J. Rieger, S. Novinski, Plastics compounding, pp. 56–58, July/August, 1984; C. J. Rieger, Soap/Cosmetics/Chemical Specialties, 56, pp. 54, 58, 70, 72, June, 1980; W. Bäumer, Parbe and Lack, 79, pp. 530–536 (1973); G. A. Möschl, Riechstoffe, Aromen, Kosmetika, 29, pp. 7–9, 13–14 (1979); G. A. Möschl, Seifen - Öle - Wachse, 106, pp. 93–98 (1980), L. C. Kingman, Jr., M. E. Kleinton, Soaps, Detergents and Toiletnes Review, 10, pp. 24–26 (1980); B. S. Durham, American Perfumes and Cosmetics, Vol. 82, pp. 31–32, July, 1967.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 40 09 567.3, filed Mar. 24, 1990, are hereby incorporated by reference.

EXAMPLES

Example 1

1 g of nickel phthalocyanine (NiPc) is dissolved in 100 ml of concentrated sulfuric acid by stirring. 9 g of Iriodin ® 100 from Merck, Darmstadt, are added to the solution and brought into suspension by stirring. After the suspension has been effected and stirring has been continued for about 15 minutes, the mixture is poured rapidly and completely into about 1 liter of ice water while stirring. The precipitating pigment coated with nickel phthalocyanine is filtered by suction, washed free from sulfate and dried at 80° C. in a drying oven. The pigment obtained in this manner is incorporated into an organic paint binder (commercial base paint from Herberts, Wuppertal) in a concentration of 7%, based on the total paint system. The result is a paint which exhibits a blue-tinged silver effect with color shift towards the blue inherent color of the NiPc.

Example 2

1 g of phthalocyanine (Pc) is dissolved in 100 ml of concentrated sulfuric acid by stirring. 9 g of the interference pigment Iriodin ® 235 from Merck, Darmstadt, are added to the solution and brought into suspension. After about 15 minutes the mixture is poured into about 1 liter of ice water. The coated pigment obtained is filtered by suction, washed free from sulfate and dried at 80° C. in a drying oven. The pearl luster pigment produced in this manner is incorporated in a clearcoat (as in Example 1) in a concentration of 7%, based on the total paint system. The result is a paint which exhibits a green pearlescent luster hue as the interference color of the Iriodin ® 235 with a color shift to the blue inherent color of phthalocyanine.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An effect pigment comprising an interference pigment coated with a metal-free phthalocyanine or metal phthalocyanine dye, wherein the dye is a film directly adhering to the interference pigment without a binder system or auxiliary material.

2. An effect pigment according to claim 1, wherein the interference pigment is a pearl luster pigment.

3. An effect pigment according to claim 2, wherein the pigment is a metal flake coated with a metal oxide that is at least one of $TiO_2$, $Fe_2O_3$, $SnO_2$, $Cr_2O_3$, or ZnO.

4. An effect pigment according to claim 1, wherein the dye is metal-free phthalocyanine.

5. An effect pigment according to claim 1, wherein the dye is nickel phthalocyanine.

6. A process for the production of an effect pigment comprising an interference pigment coated with a metal-free phthalocyanine or metal phthalocyanine dye, said process consisting essentially of combining a suspension of an interference pigment in a solution of the dye with a solvent in which the dye is essentially insoluble, so that the dye is deposited onto the pigment, whereby in the resultant effect pigment the dye forms a film directly adhering to the interference pigment without a binder system or auxiliary material.

7. A process, for preparing an effect pigment according to claim 6, wherein the interference pigment is a mica flake coated with at least one metal oxide.

8. A process for preparing an effect pigment according to claim 7, wherein the metal oxide is at least one of $TiO_2$, $Fe_2O_3$, $SnO_2$, $Cr_2O_3$ or ZnO.

9. A process for preparing an effect pigment according to claim 6, wherein the dye is metal-free phthalocyanine.

10. A process for preparing an effect pigment according to claim 6, wherein the dye is nickel phthalocyanine.

11. A process according to claim 9, wherein the phthalocyanine is in solution in sulfuric acid.

12. A process for preparing an effect pigment according to claim 11, wherein the phthalocyanine solution is combined with water.

13. An effect pigment prepared according to claim 6.

14. In a paint, dye, plastic or cosmetic formulation comprising an effect pigment which is an interference pigment coated with a metal-free phthalocyanine or metal phthalocyanine dye, the improvement wherein the effect pigment is one according to claim 1.

15. In a paint, dye, plastic or cosmetic formulation comprising an effect pigment which is an interference pigment coated with a metal-free phthalocyanine or metal phthalocyanine dye, the improvement wherein the effect pigment is one prepared according to claim 6.

* * * * *